(12) United States Patent
Coquoz et al.

(10) Patent No.: US 7,555,334 B2
(45) Date of Patent: Jun. 30, 2009

(54) SMALL ANIMAL LIGHT INTENSITY MONITOR

(75) Inventors: Olivier Coquoz, Oakland, CA (US); Bradley W. Rice, Danville, CA (US); David G. Nilson, Walnut Creek, CA (US); Michael D. Cable, Danville, CA (US)

(73) Assignee: Xenogen Corporation, Alameda, CA (US)

(*) Notice: Subject to any disclaimer, the term of this patent is extended or adjusted under 35 U.S.C. 154(b) by 991 days.

(21) Appl. No.: 10/969,230

(22) Filed: Oct. 19, 2004

(65) Prior Publication Data

US 2005/0175538 A1 Aug. 11, 2005

Related U.S. Application Data

(60) Provisional application No. 60/513,179, filed on Oct. 20, 2003.

(51) Int. Cl.
*A61B 6/00* (2006.01)
*A61K 49/00* (2006.01)
(52) U.S. Cl. ........................ 600/476; 424/9.1
(58) Field of Classification Search .............. 600/473, 600/476; 119/729, 809, 417, 830; 422/52; 436/172
See application file for complete search history.

(56) References Cited

U.S. PATENT DOCUMENTS

| | | | |
|---|---|---|---|
| 3,739,751 A * | 6/1973 | Mohr et al. ................ 119/752 |
| 4,149,249 A * | 4/1979 | Pavkovich ................... 378/14 |
| 5,167,160 A * | 12/1992 | Hall, II ..................... 73/864.91 |
| 5,321,261 A | 6/1994 | Valenta ..................... 250/252.1 |
| 5,637,874 A * | 6/1997 | Honzawa et al. ......... 250/361 C |
| 5,650,135 A * | 7/1997 | Contag et al. ............... 424/9.1 |
| 5,653,940 A | 8/1997 | Carey et al. .................. 422/52 |
| 5,837,195 A | 11/1998 | Malek et al. ................. 422/52 |
| 5,927,234 A * | 7/1999 | Siegel ......................... 119/751 |
| 6,242,743 B1 | 6/2001 | DeVito et al. ........... 250/363.05 |
| 6,377,342 B1 | 4/2002 | Coeurveille ................ 356/244 |
| 6,789,510 B1 * | 9/2004 | Lee ............................. 119/811 |
| 7,366,333 B2 * | 4/2008 | Long et al. .................. 382/128 |
| 2002/0114765 A1 * | 8/2002 | Grable et al. ................ 424/9.6 |

* cited by examiner

*Primary Examiner*—Eric F Winakur
*Assistant Examiner*—Helene Bor
(74) *Attorney, Agent, or Firm*—Beyer Law Group LLP

(57) ABSTRACT

Disclosed are methods and apparatus for collecting light emitted from an animal, where a luminescent reporter has been injected into the animal is disclosed. The apparatus includes a chamber for receiving the animal, wherein the chamber is light tight preventing a substantial portion of light emitted from the animal from escaping the chamber when the chamber is closed and the animal is inside the chamber and a light monitoring device for collecting light from different portions of the animal when the animal is inside the closed chamber. The light monitoring device is arranged to collect light over substantially the entire surface area of the body and head of the animal, and the light monitoring device generates a quantified value based on the light collected from the animal. The animal does not have to be under anesthesia.

23 Claims, 8 Drawing Sheets

SMALL ANIMAL LIGHT INTENSITY MONITOR

CROSS-REFERENCE TO RELATED APPLICATION

This application claims priority under 35 U.S.C. §119(e) from co-pending U.S. Provisional Patent Application No. 60/513,179 filed on Oct. 20, 2003 entitled "SMALL ANIMAL LIGHT INTENSITY MONITOR" by Coquoz, et al., which is incorporated by reference for all purposes.

FIELD OF THE INVENTION

The present invention relates generally to studying the health of an animal over time using bioluminescent techniques, where a luminescent reporter has been injected into the animal. In particular, the present invention relates to systems and methods for detecting light emitted from a living small animal in response to a biological effect in such animal, which is particularly useful in biomedical and research applications.

BACKGROUND OF THE INVENTION

Bioluminescence is a non-invasive technique for performing in vivo diagnostic studies on animal subjects in the areas of medical research, pathology and drug discovery and development. Bioluminescence is typically produced by cells that have been transfected with a luminescent reporter such as luciferase and can be used as a marker to differentiate a specific tissue type (e.g. a tumor), monitor physiological function, track the distribution of a therapeutic compound administered to the subject, or the progression of a disease. A wide range of applications have been demonstrated including areas of oncology, infectious disease, and transgenic animals.

Photons emitted by bioluminescent cells are strongly scattered in the tissue of the subject such that propagation is diffusive in nature. As photons diffuse through tissue many are absorbed, but a fraction reach the surface of the subject and can be detected. In general, absorption in mammalian tissues is high in the blue-green part of the spectrum (<600 nm) and low in the red and NIR part of the spectrum (600-900 nm). Firefly luciferase has a rather broad emission spectrum ranging from 500-700 nm, so at least part of the emission is in the low absorption region. Since the mean-free-path for scattering in tissue is short, on the order of ~0.5 mm, photons from deep sources are scattered many times before reaching the surface.

One bioluminescent application is referred to as bioluminescent imaging. Such bioluminescent imaging systems effectively record the spatial distribution of these photons emitted from the surface of the subject. Some specialized in-vivo imaging applications may include analysis of one or more representations of emissions from internal portions of a specimen superimposed on a photographic representation of the specimen. The photographic representation provides the user with a pictorial reference of the specimen. The luminescence representation indicates portions of the specimen where an activity of interest may be taking place.

Obtaining the luminescence representation may involve image capture over an extended period of time, e.g., minutes. The living specimen is typically anesthetized during this time to prevent movement that may compromise image capture. Accordingly, these imaging systems require complex anesthesia delivery systems to deliver anesthesia gases to the specimen. Additionally, such luminescence imaging systems tend to be expensive and difficult to maintain. All these factors result in low throughput for analyzing specimens.

Hence, there is interest in developing both improved luminescence detection systems that would provide simple and efficient low cost systems, which do not require anesthesia for the specimen.

SUMMARY OF THE INVENTION

Accordingly, mechanisms are provided for uniformly collecting light over the surface of a living animal that is not under anesthesia and obtaining a quantitative measurement of the collected light. The light is collected from the animal without generating an image based on such collected light. Preferably, the light is collected over substantially the entire surface of the animal in less than 60 seconds, but the exposure time can be as short as 2 seconds and still quantify the total amount of light emitted from the entire body. The quantitative measurement of the collected light may be in the form of a photon count and/or a current measurement based on the photons emitted and detected from the animal.

The light monitoring mechanisms of the present invention allows rapid and low cost assessment of a specimen in particular applications, where a quantitative measurement of light emission from the specimen is all that is required. For example, when certain transgenic animals are given a particular toxin, light is always expressed in the liver. Thus, one simply can detect an increase in light emission from this type of mouse as a whole to determine the presence of this particular toxin without the need for generation of an image of the light emission for such mouse. Such a low cost light monitoring system also is highly scalable. Additionally, since the light monitoring mechanisms of the present invention allow rapid detection of light output from the animal (e.g., within a few seconds), the animal does not have to be put under anesthesia, which is advantageous in certain biological research applications. For instance, the animal may be monitored several times a day for deviations in light emission since the animal does not have to undergo anesthesia, whereas frequent anesthesia of the animal would otherwise adversely affect the physiology of the animal.

In one embodiment, an apparatus for collecting light emitted from an animal, where a luminescent reporter has been injected into the animal, is disclosed. The apparatus includes a chamber for receiving the animal and a light monitoring device for collecting light from different portions of the animal when the animal is inside the closed chamber. The chamber is light tight to prevent outside room light from entering the chamber when the chamber is closed and the animal is inside the chamber. The light monitoring device is arranged to collect light over substantially the entire surface area of the body and head of the animal, and the light monitoring device generates a quantified value based on the light collected from the animal. Using the apparatus of the present invention, the animal does not have to be under anesthesia.

In a specific implementation, the light emitted from the animal has a surface radiance between about $10^3$ to about $10^{10}$ photons/second/squared centimeter/steradian. In another aspect, the light monitoring device is configured to collect light over substantially the entire surface area of the body and the head of the animal in less than 60 seconds. In one example embodiment, the light monitoring device includes a plurality of sensors (e.g., photomultiplier tubes or PMT's) arranged over various overlapping areas of the animal and/or a first movement mechanism for moving the sensors over the surface area of the animal. In a further aspect, the light monitoring device further includes a second movement mechanism for positioning the sensors with respect to the animal so that the animal is in either a first position wherein the sensors can collect light from the animal or a second position wherein the sensors cannot collect a substantial portion of the light from the animal. For instance, the first position is located between the sensors and the second position is located outside the sensors. In this embodiment, the light monitoring device further includes a restrainer for holding the animal in a substantially fixed, resting horizontal position while the animal is positioned in the first position and the sensors are collecting light from the animal.

In one aspect, the first movement mechanisms is a rotation motor for rotating the sensors around the longitudinal axis of the animal while the animal is held by the restrainer and after the animal is positioned in the first position by the second movement mechanism. In this aspect, the second movement mechanism is a translation motor.

In one aspect, the restrainer is formed from a material that can be sterilized at high temperatures and high pressure, such as a glass material. In a specific implementation, the restrainer has a glass tube for inserting the animal therein and holding the animal's body in a substantially fixed, resting horizontal position. The glass tube includes a nose holding device which can flexibly conform to a portion of the animal's head to thereby hold the animal head in a substantially fixed, resting horizontal position. The restrainer further includes a tail holding portion for holding the animal's tail in a substantially fixed position. In one aspect, the tail holding portion includes a groove for receiving the tail of the animal and one or more straps for holding the tail within the groove.

In one example, the sensors are staggered along the longitudinal axis of the animal. The sensors are also preferably spaced an equal distance apart around the longitudinal axis of the body and head of the animal. In a specific implementation, there are three sensors spaced 120 degrees apart around the longitudinal axis of the animal.

In another aspect, the invention pertains to a method of collecting light emitted from an animal, where a luminescent reporter has been injected into the animal. The animal is placed in a restrainer so that the animal is held in a substantially fixed, resting horizontal position. A plurality of detectors are then moved relative to the animal from a home position to a measurement position. A 360 degree rotation of the detectors is launched around the animal. A quantitative measurement is obtained based on light detected by the detectors. In one embodiment, after the detectors are launched, they detect light continuously as the detectors rotate 360 degrees around the animal. In another embodiment, after the detectors are launched, they detect light at discrete positions around the 360 degrees, wherein movement of the detectors is stopped at each discrete position. In yet a final embodiment, the following procedures are implemented based on a mode selection: (a) after the detectors are launched, they detect light continuously as the detectors rotate 360 degrees around the animal when a continuous mode is selected and (b) after the detectors are launched, they detect light at discrete positions around the 360 degrees, wherein movement of the detectors is stopped at each discrete position when a stepping mode is selected.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
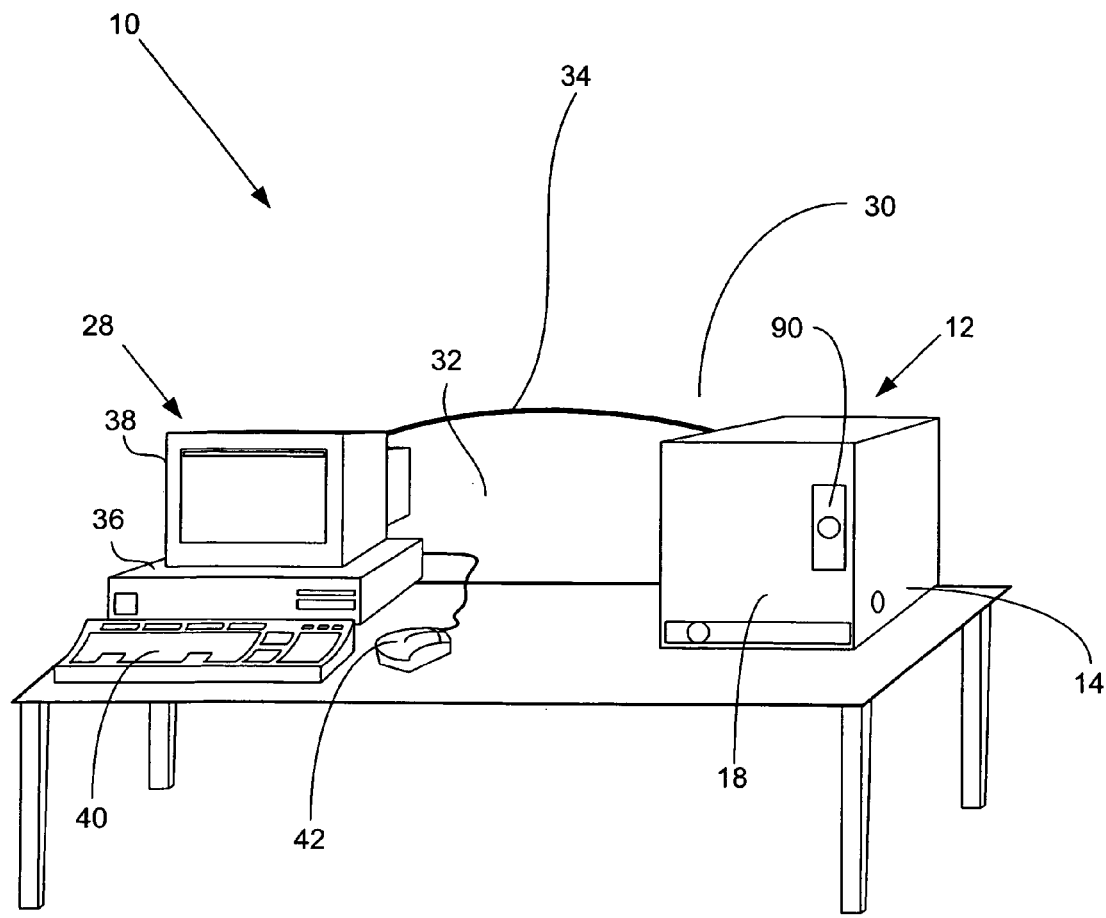
FIG. 1 is a perspective view of a light monitoring system adapted to rapidly detect light emitted from a specimen in accordance with one embodiment of the invention.

The light monitor of the present invention may be implemented within any suitable system for facilitating rapid collection and quantization of light emitted from a small animal. FIG. 1 illustrates a light monitor system 10 adapted to rapidly measure light emitted from an animal in accordance with one embodiment of the present invention. The system 10 generally detects and processes low intensity light sources emitted from a small animal. For example, the light monitor system detects light emitted from the animal and converts the light into a quantified value, such as a photon count and/or a current value.

Light refers to photons and electromagnetic energy anywhere in the visible to near-infrared (NIR) part of the spectrum in the wavelength range of 400-950 nm. It is understood that some intensities detected and processed in system 10 are not readily detectable by human vision. For example, low intensity light emitted from an animal may have a surface radiance between about $10^3$ to about $10^{10}$ photons/second/squared centimeter/steradian, where the lower end of this range is typically well below human eye detection levels.

In the illustrated embodiment, the light monitor system 10 includes a chamber 12 adapted to receive a light-emitting specimen, such as a small animal, in which low intensity light, e.g., luciferase-based luminescence, is to be detected by a light intensity monitor device (not shown) located within the chamber 12 or coupled with the chamber 12. Preferably, the chamber 12 is light tight for preventing outside room light from entering the chamber and interfering with light emitted from the animal during imaging. Further description of light tight designs suitable for use with the present invention are described in commonly-owned pending U.S. patent application having Ser. No. 09/795,056, filed Feb. 21, 2001, entitled IMPROVED IMAGING APPARATUS, by Michael D. Cable et al., which application is incorporated herein by reference in its entirety for all purposes.

A computer 28 is in communication with various components, such as the light intensity monitor (not shown) in the chamber 12 via cable 34. One implementation of a computer is further described below with respect to FIG. 8. Alternatively, a computer or processing and memory components may be integrated with the light monitor equipment to form a single unit.

Computer 28 may be implemented with any suitable combination of hardware and software for controlling and monitoring any of the devices in system 10. Components controlled by the computer 28 may include the light monitor device, one or more motors for moving the light monitor devices relative to the specimen, and one or more motors for moving the specimen with respect to chamber 12 (e.g., via a movable stage for holding the specimen). Computer 28 also communicates with a display 38 for presenting detected light information collected from light monitoring devices to the user and may also act an interface to control the light monitor system 10.

Figure 2:
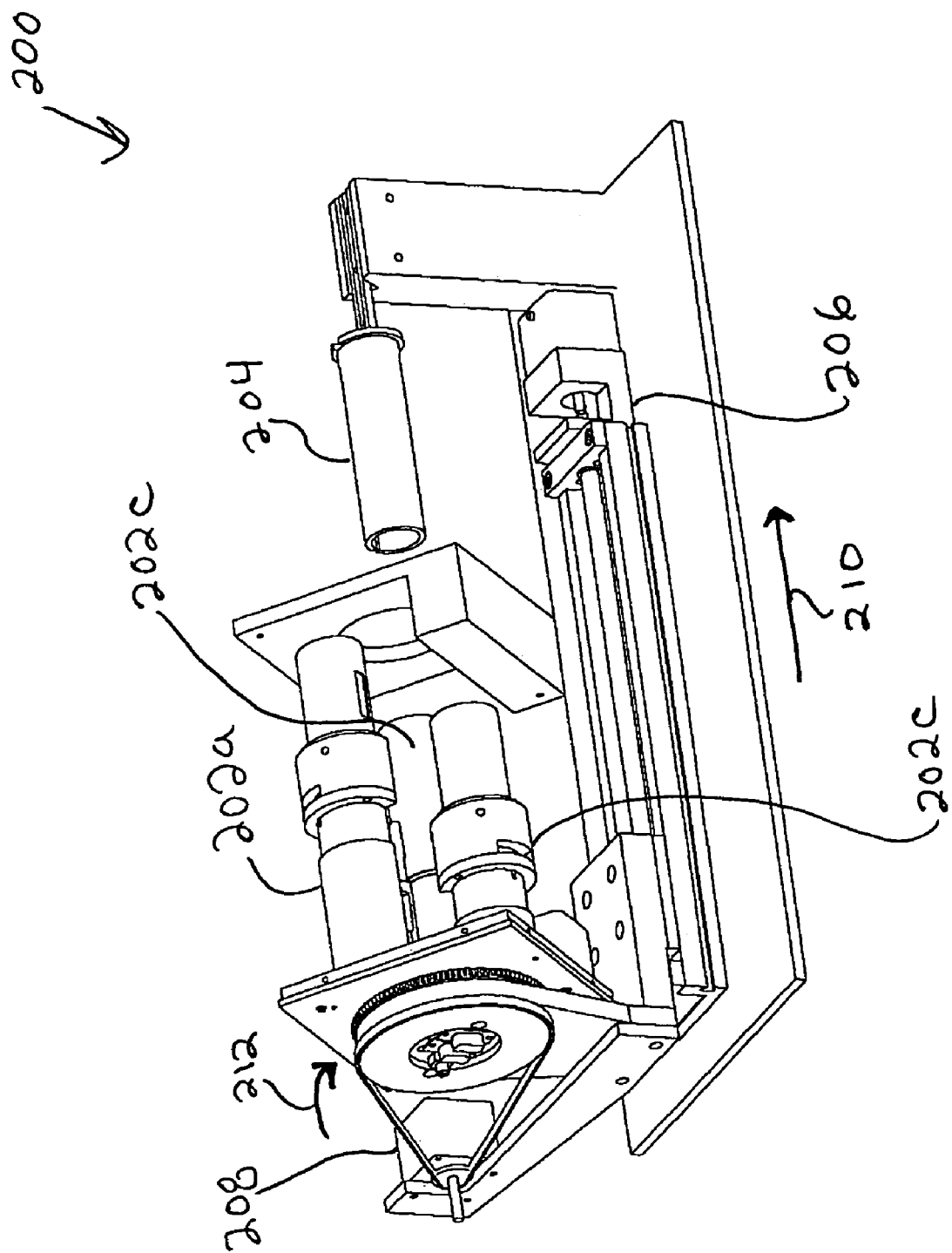
FIG. 2 is a perspective view of a light monitoring device in accordance with one embodiment of the present invention.

FIG. 2 is a perspective view of a light monitoring device 200 in accordance with one embodiment of the present invention. As shown, the monitoring device 200 includes one or more light sensors 202 for collecting light from the animal, an animal restrainer 204 for holding the animal, a translation motor 206, and a rotation motor 208. The light sensors 202 may take any suitable form for collecting light or photons emitted from the animal. In a preferred embodiment, each light sensor is in the form of a Photo Multiplier Tube (PMT), a silicon photodiode, an avalanche photodiode (APD), or a hybrid PMT. The restrainer 204 may take any suitable form for holding the animal in a fixed position while light is collected by the sensors 202.

The monitoring system 200 may have any suitable number and type of movement mechanisms or motors for positioning the restrainer 204 relative to the sensors 202. In the illustrated embodiment, the translation motor 206 is operable to move the sensors 202 in translational direction 210 towards and away from the restrainer 204. Alternatively, the translation motor 206 may be arranged to move the restrainer towards and away from the sensors 204 and animal located thereon. By way of examples, the translation motor 206 may be in the form of a stepper motor and linear slide, from Thomson Industries, model number MS33LHAL. This translation movement could also be achieved with the use of a DC motor. Alternatively, the translation motor may be removed and the restrainer 204 and animal may be set in a fixed measurement position relative to the sensors 202. The animal is then placed within the restrainer and immediately ready for measurement by the fixed position sensors without movement of the restrainer or sensors.

In the illustrated embodiment, the rotation motor 208 is generally operable to rotate the sensors 202 in direction 212 around restrainer 204 when the restrainer contains the animal and is located between the sensors. In one embodiment, the rotation motor includes a gear and teeth arrangement coupled with a stepper motor for rotating the sensors around the animal. By way of examples, the rotation motor may be implemented by a stepper motor or a low-noise DC motor.

Figure 3:
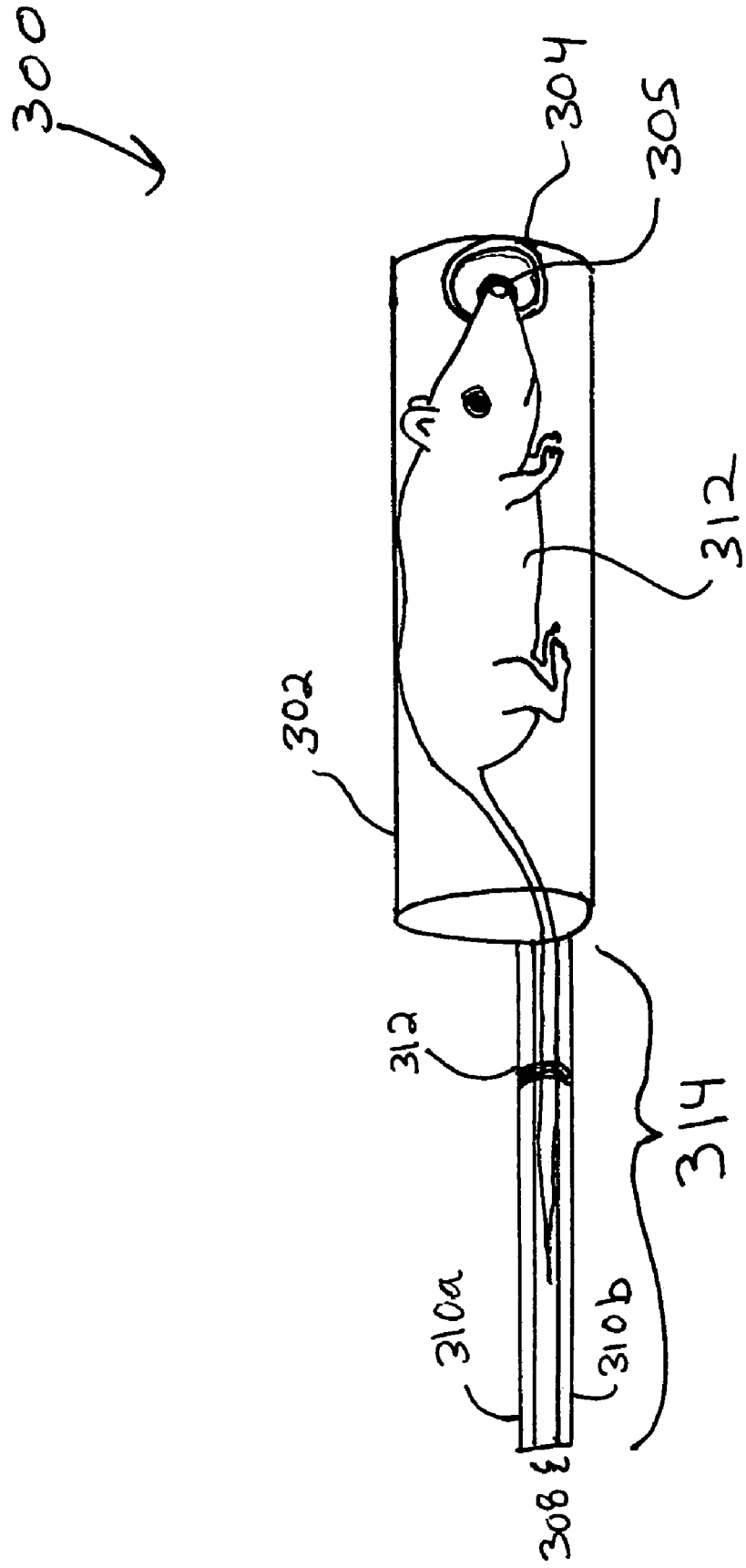
FIG. 3 is a diagrammatic representation of an animal restrainer for holding a small animal in accordance with one embodiment of the present invention.

FIG. 3 is a diagrammatic representation of an animal restrainer 300 containing a small animal 312 in accordance with one embodiment of the present invention. In this example, the small animal 312 is a mouse. The restrainer 300 preferably holds the mouse a at substantially fixed position during the light collection operation and is easily sterilized at high temperatures and high pressure, e.g., 140~177° C. and 3 bars. In the illustrated embodiment, the restrainer 300 includes a glass tube 302 into which the mouse 312 is inserted. The tube facilitates keeping the mouse in a substantially fixed position.

The glass tube 302 has a plastic cup or cone 304 for holding the mouse's head in a fixed position. Of course, any suitably shaped nose holding structure may be used. Other materials which may be used to form the nose holding structure include Delrin and Polycarbonate. In the illustrated embodiment, the plastic cup 304 has an indention 305 into which the mouse's nose is inserted. Preferably, the cup 304 has a hole within the indention so that the mouse can breath while it is being restrained.

As shown, the restrainer 300 also includes a tail holder portion 314 for holding the animal's tail. As shown, the tail holder portion 314 includes raised edges 310a and 310b which defines a groove 308 into which the mouse's tail is positioned. The tail holder 314 also includes one or more straps 312 for holding the mouse's tail in place. In an alternative embodiment, the animal is confined to a measurement chamber of any suitable size or shape so as to constrain the animal's movement while allowing insertion of the animal into the measurement chamber. For example, the measurement chamber is sized to be slightly larger than a typical mouse.

Figure 4:
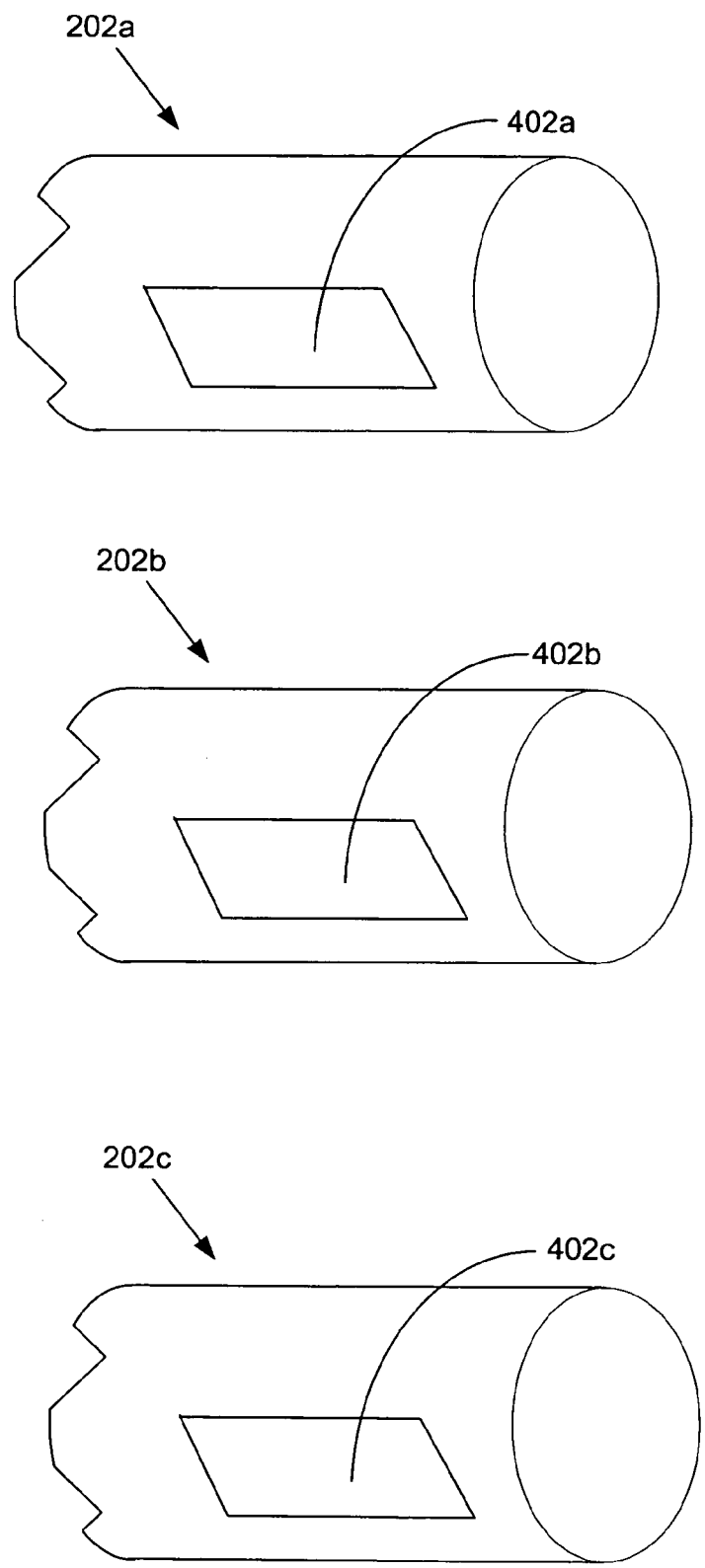
FIG. 4 is a diagrammatic representation of the end portions of the PMT's of FIG. 2 in accordance with one embodiment of the present invention.

Referring back to the embodiment of FIG. 2, there are three PMT's which may be positioned around the restrainer 204 when the restrainer is moved into a measurement position. Of course, there may be any suitable number of PMT's, which depends on the particular application. FIG. 4 is a diagrammatic representation of the end portions of the PMT's 202a through 202c of FIG. 2 in accordance with one embodiment of the present invention. As shown, each PMT 202 includes a sensing area 402. For example, PMT 202a includes sensing area 402a; PMT 202b includes sensing area 402b; and PMT 202c includes sensing area 402c. As shown, each sensing area 402 is in the form of a rectangular area, which is about 24 mm by 8 mm in size although the sensing area may be any suitable size and shape.

When the animal is moved into the position for measurement, the PMT's are preferably staggered along the longitudinal axis of the animal and rotated around such axis so as to provide uniform light collection along the longitudinal axis of the animal and at all angles around the animal. In one arrangement, the PMT's may be placed so that their sensitive area are positioned at a distance that is equal to about 1 mm from each other and a distance of about 15-20 mm from the animal surface. The number of PMT's selected depend on the desired trade-off between system complexity and uniformity of light collection coverage. The system of the present invention may also easily be scaled up or down for differently sized animals.

Figure 5A:
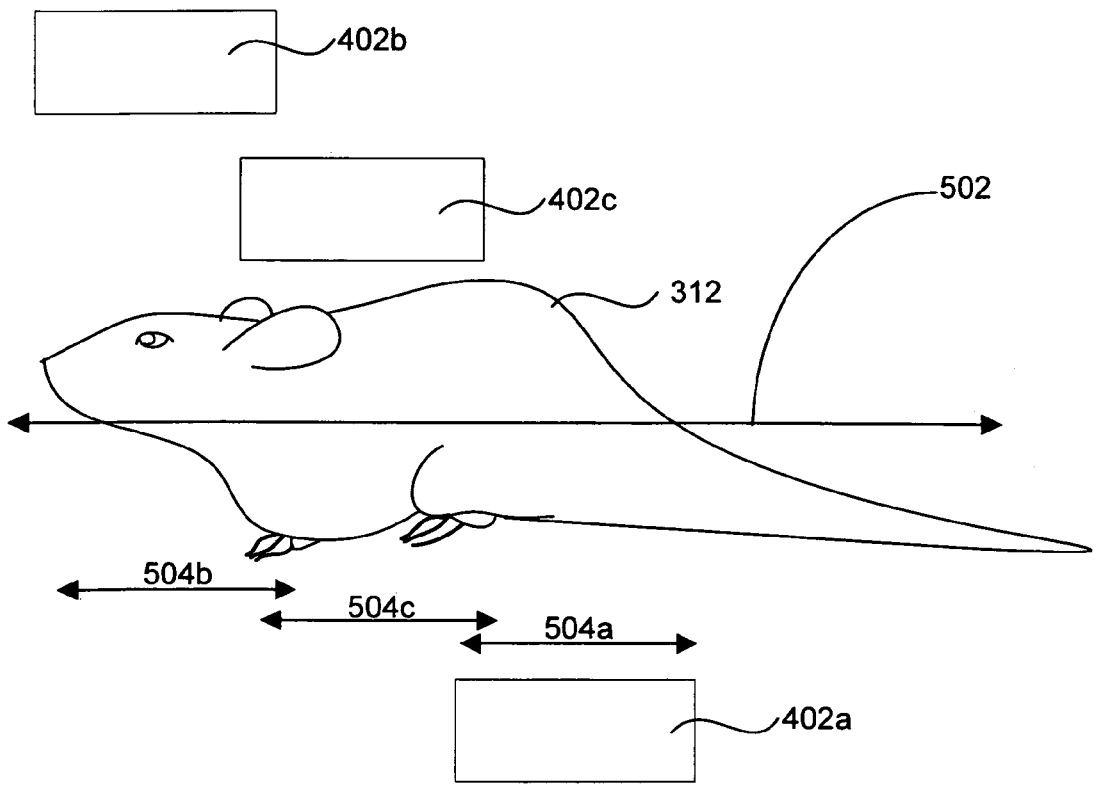
FIGS. 5A and 5B illustrate example positions of three PMT's relative to a small animal in accordance with one embodiment of the present invention.
Figure 5B:
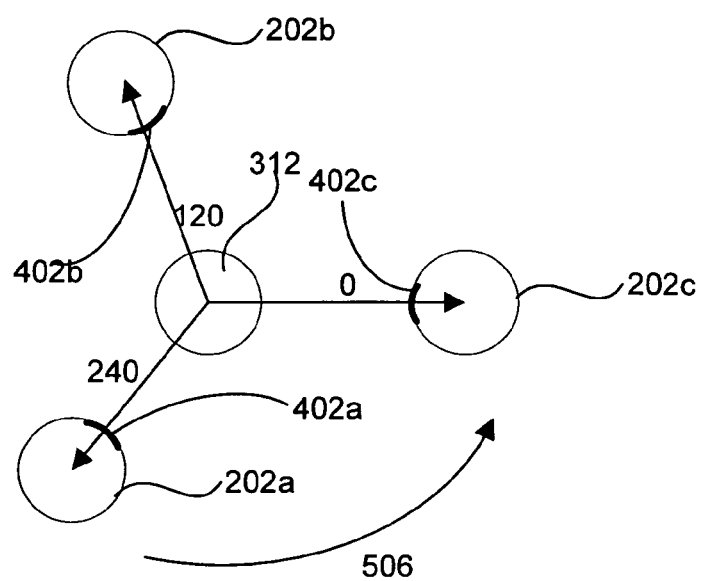

FIGS. 5A and 5B illustrate example positions of three PMT's relative to a mouse in accordance with one embodiment of the present invention. FIG. 5A Illustrates a side view of the animal 312 and the relative positions of PMT's 402a, 402b, and 402c along a longitudinal axis 502 of the mouse 312. Accordingly, the PMT's are operable to detect light emitted from different segments of the mouse 312 along the longitudinal axis 502. As shown, PMT 402a detects light from the longitudinal portion 504a; PMT 402b detects lights from the longitudinal portion 504b; and PMT 402c detects light along the longitudinal portion 504b. Alternatively, the sensors may be arranged to detect light from only specific regions of the animal, e.g., to reduce noise or focus on a specific regions of the animal such as the head or liver region.

FIG. 5B illustrates an end view of the PMT's where a longitudinal axis of the animal 312 is perpendicular to the page. The PMT's may be arranged in any suitable manner so as to detect photons emitted from this animal 312. Some of the factors to consider in PMT configuration are light detection efficiency and cost. In one preferred embodiment, the PMT's are evenly spaced around the longitudinal axis of the body and head of the animal, e.g., 120 degrees apart. As shown, PMT 202c is placed at 0 degrees with sensing area 402c facing toward the mouse 312. With PMT 202c at 0 degress, PMT 202b is positioned at 120 degrees with sensing area 402b facing toward the mouse 312, while PMT 202a is positioned at 240 degrees with sensing area 402a facing toward the animal 312. The PMT's are operable to rotate in direction 506, for example. Of course, the PMT's may rotate in either a clockwise or counter clockwise fashion.

Figure 6:
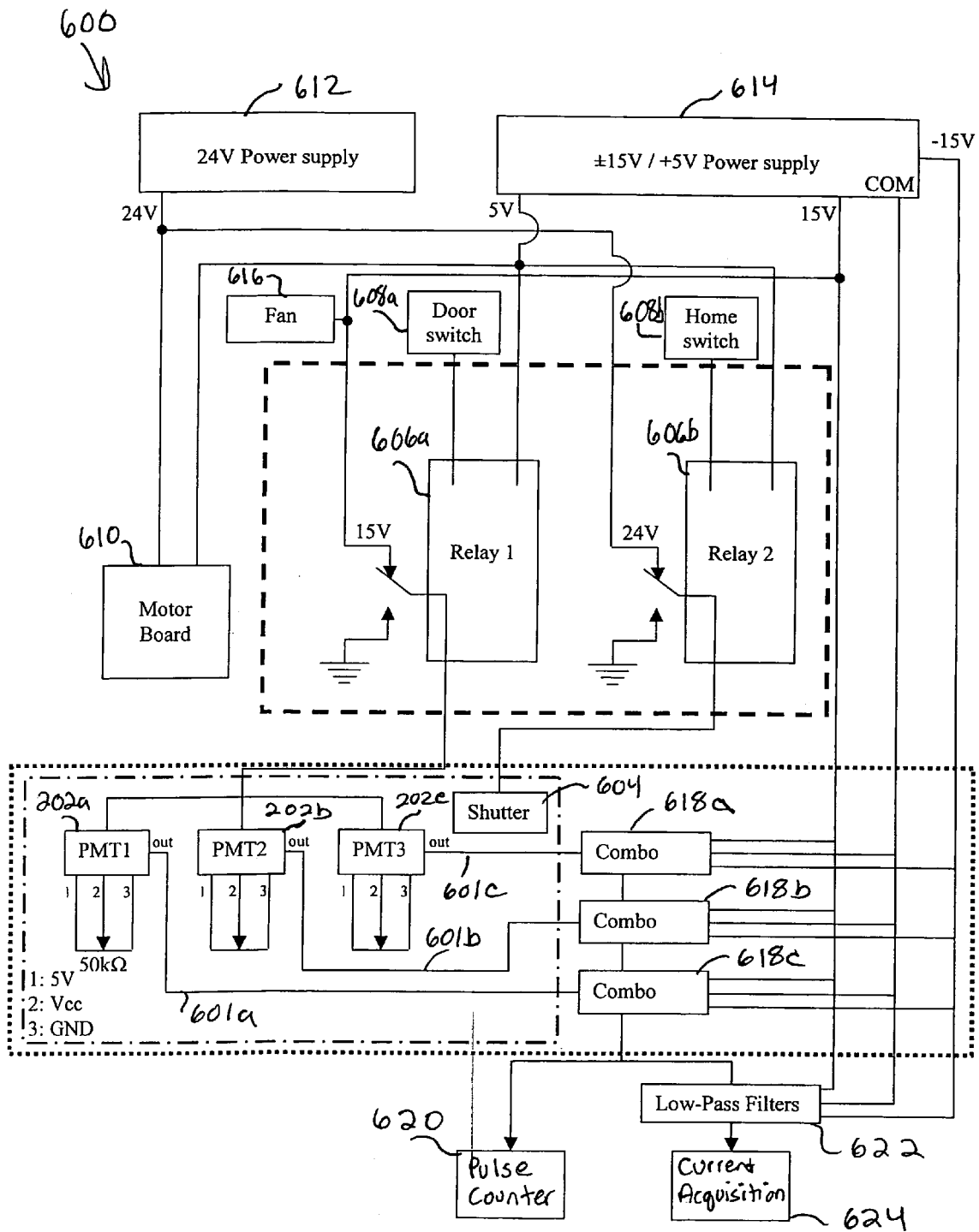
FIG. 6 is a schematic electrical diagram of a light monitoring system in accordance with a specific implementation of the present invention.

FIG. 6 is a schematic electrical diagram of a light monitoring system 600 in accordance with a specific implementation of the present invention. As shown, there are three PMT's 202a through 202c. As is well known to those skilled in the art, each PMT is coupled to a 50 k ohm potentiometer used to tune each detector's gain. Each PMT also outputs detected light in the form of an electron pulse signal 601. As, shown, PMT 202a outputs pulse signals 601a; PMT 202b outputs pulse signal 601b; and PMT 202c outputs pulse signal 601c. These electron pulse signals are in the form of pulses which each correspond to one or more photons emitted from the animal.

The pulse signal may be analyzed and quantified. By way of examples, the pulses may be used to obtain a photon count and/or averaged to obtain an average or DC current value. The monitoring device 600 often includes one or more combination blocks 618 for formatting the pulse signals. In the illustrated embodiment, each combination circuit 618 operates to format the pulses so that they may then be counted by pulse counter 620, as well as averaging the output current so that it may be filtered through low pass filter 622 and acquired through current acquisition block 624.

The monitoring system 600 may include any suitable safety mechanism for preventing outside light from inadvertently reaching the PMT's 202 sensor which may saturate and damage the PMT. As shown, the monitoring systems 600 includes shutter 604 which is closed by home switch 608b via relay 606b when the animal is positioned in the home position away from the PMT's. The shutter is opened when the animal is positioned in the measurement position and moved away from the home position. Additionally, the monitoring system 600 includes a door switch 608a which operates via relay 606a to turn off this PMT's 202 when the chamber door is open.

The monitoring systems 600 may include any number and type of power supplies, e.g., a 24 volt power supply 612 and a 15 volt and 5 volt power supply 614 for supplying power to the various components of the monitoring device 600. The monitoring system 600 may also include a fan 616 for cooling the electronics.

As illustrated in more detail in FIG. 2, the monitoring system 600 also includes one or more motors driven by the motor board 610 for rotating the sensors around the animal and translating the restrainer and animal to a measurement position as described above.

Figure 7:
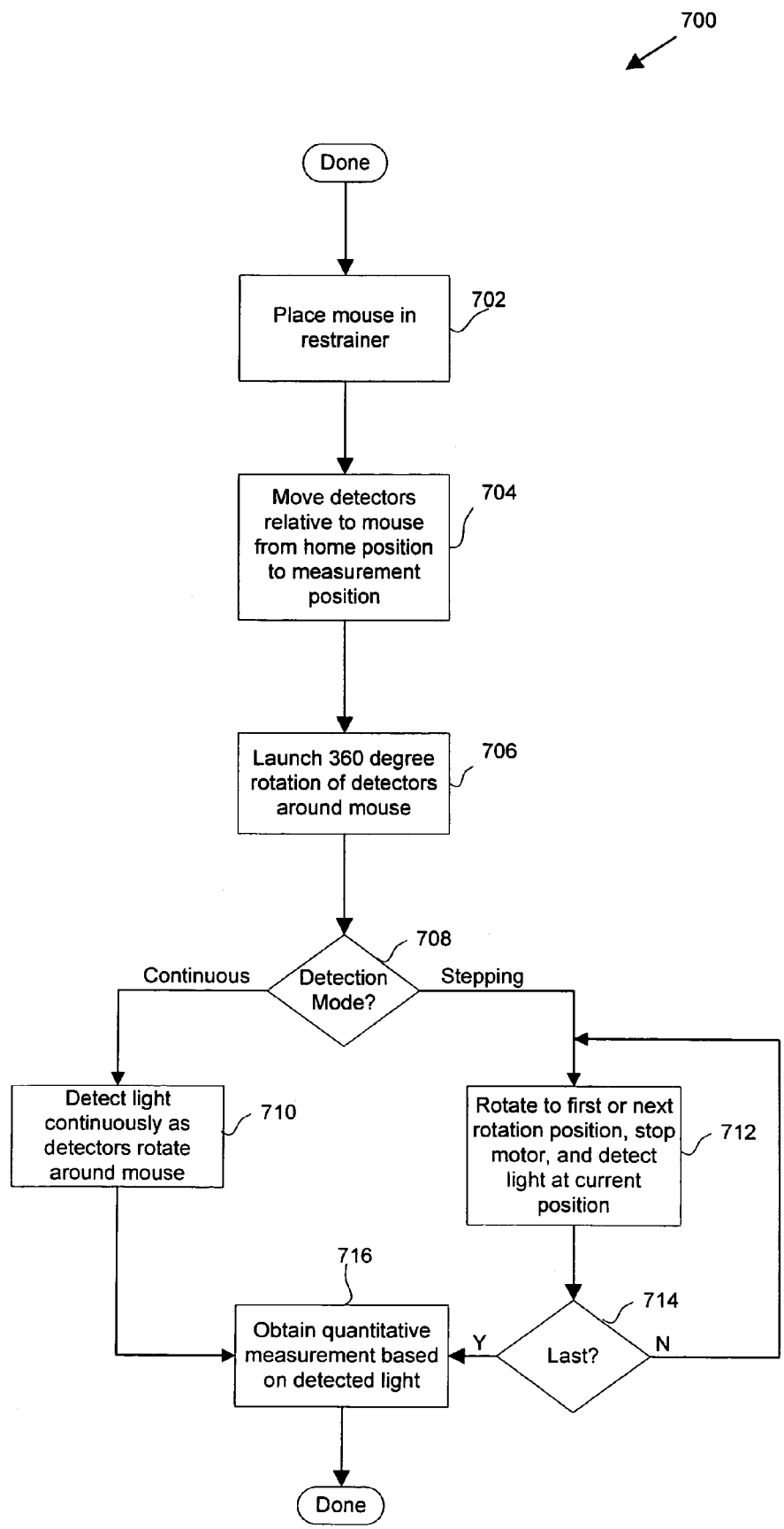
FIG. 7 is a flowchart illustrating a procedure for monitoring light emitted from a small animal in accordance with one embodiment of the present invention

FIG. 7 is a flowchart illustrating a procedure 700 for monitoring light emitted from a small animal using a light monitoring system in accordance with one embodiment of the present invention. Initially, the mouse (or other animal) is placed in a restrainer, such as the restrainer 300 of FIG. 3, in operation 702. The detectors or sensors are then moved relative to the mouse from a home position to a measurement position in operation 704. A 360 degree rotation of the detectors is then launched around the mouse in operation 706. It is then determined which detection mode has been selected in operation 708. Of course, the light monitoring system may only be capable of one mode, where operation 708 would be skipped.

When a continuous mode is selected, light is continuously detected as the detectors rotate continuously around the mouse in operation 710. If a stepping mode is selected, the detectors are moved in a stepping fashion. Accordingly, the detectors are initially rotated to a first rotation position; the motors are stopped; and light is detected at the current position in operation 712. It is then determined whether the last position has been reached in operation 714. Otherwise, the motors rotate to a next rotation position, stop, and light is detected at the current position in operation 712. The motors continue to incrementally start and stop around the 360 degree of rotation positions in operation 712 until the last position is reached. When the last position is reached, in the stepping or continuous mode, a quantitative measurement is then obtained based on the detected light in operation 716. The procedure 700 for light monitoring is then complete. For example, the total amount of detected light is quantified as a photon count or a current total or average value.

Either mode may be utilized to collect light from the animal. In one example, the detectors are operated in a photon counting mode when signals to be detected are very dim, and the detectors are operated in a current averaging mode when signals to be detected are bright and can possibly reach a level that would cause saturation in the photon counting mode. In a specific implementation, the photon counting mode is used for a light emission range between about 50 to 1e6 cps (counts per second), and the current mode is used for 180 to 2.7e7 cps. With a conversion factor of 9000 photons/s per cps, a photon counting mode is used for a light emission range between about 4.5e5 to 9e9 photons/s, and a current mode is used for about 1.62e6 to 2.43e11 photons/s. These values are valid for the specific detectors and geometries in the illustrated embodiment and will vary with other implementations.

The results of measurement and data analysis may then be used to quantify the expression of a reporter gene, or the stage of progression of cancer metastasis or infectious disease in a laboratory animal. One primary application envisioned is the validation of Light-Producing Transgenic Animals (LPTA), by monitoring quantitatively and precisely the expression of the targeted genes, this instrument can also be used for fast, high-throughput screening of infectious disease and tumor models in laboratory animals, and to the drug development projects related to them. Towards this end, the instrument are preferably accurate, fast, easy-to-use, and the animals do not require anesthesia.

In general terms, the amount of light emitted from the animal is directly proportional to the number of cells, bacteria, or genes which are tagged with luciferase. Accordingly, one can quantify the amount of light detected to obtain a quantitative measurement of the number of cells (e.g., in a tumor), bacteria (e.g., infection), or genes expressed. The amount of light produced per cell can be quantified by doing in vitro studies. However, since cells or bacteria or genes are typically buried deep inside living tissue which scatters and absorbs light, relative count is usually obtained (rather than an absolute count), which in most applications is sufficient.

Figure 8:
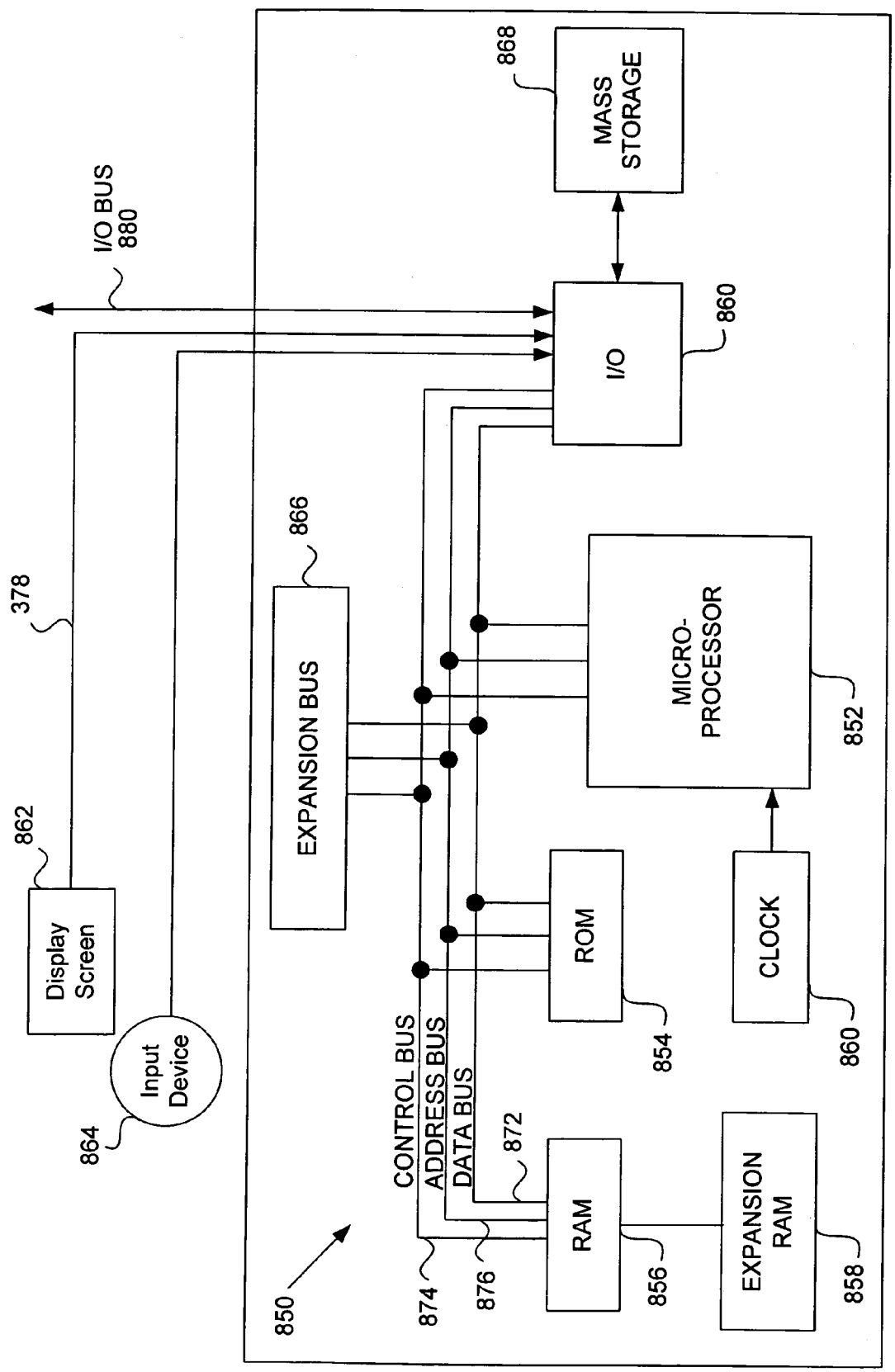
FIG. 8 illustrates an exemplary computer system in accordance with one embodiment of the present invention.

The light monitoring techniques of the present invention will typically be implemented by a suitable processor or computer-based apparatus. Referring to FIG. 8, an exemplary computer system 850 includes a central processing unit (CPU) 852, read only memory (ROM) 854, random access memory (RAM) 856, expansion RAM 858, input/output (I/O) circuitry 860, display assembly 862, input device 864, and expansion bus 866. Computer system 850 may also optionally include a mass storage unit 868 such as a disk drive unit or nonvolatile memory such as flash memory and a real-time clock 860.

Regardless of the computer system configuration, it may employ one or more memories or memory modules configured to store program instructions for detecting photons or current from a luminescent specimen and other functions of the present invention described herein. Such memory or memories may also be configured to store data structures, luminosity and current data, or other specific non-program information described herein.

Because such information and program instructions may be employed to implement the systems/methods described herein, the present invention relates to machine-readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave traveling over an appropriate medium such as airwaves, optical lines, electric lines, etc. Examples of program instructions include both machine code, such as produced by a compiler, and files containing higher level code that may be executed by the computer using an interpreter.

It should be borne in mind that although computer system 28 is discussed in some detail herein to facilitate discussion, the invention may be practiced using a variety of suitable computer-implemented techniques. In general, any suitable computer system may be employed for rapidly collecting and quantifying light emitted from a specimen. Further, the inventive light collection techniques disclosed herein may be implemented via a computer network, such as a local area network (LAN), wide area network (WAN) or a global computer network such as the Internet. In the latter cases, the collection techniques may be implemented at least in part as downloadable computer software and data (e.g., applets such as JAVA™ applets from Sun Microsystems Inc.). The downloadable computer software and data may be kept on one or more servers on the network, accessible by any client computer or terminal capable and authorized for such access. Network computing techniques and implementations are well known in the art and are not discussed in great detail here for brevity's sake.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. An apparatus for collecting light emitted from an animal, where a luminescent reporter has been injected into the animal, the apparatus comprising:

a chamber for receiving the animal, wherein the chamber is light tight preventing a substantial portion of outside room light from entering the chamber and interfering with light emitted from the animal when the chamber is closed and the animal is inside the chamber; and a light monitoring device for collecting light from different portions of the animal when the animal is inside the closed chamber, wherein the light monitoring device is arranged to rotate around and collect light over a substantially entire surface area of the body and head of the animal, wherein the light emitted from the animal has a surface radiance between about $10^3$ to about $10^{10}$ photons/second/squared centimeter/steradian, and wherein the light monitoring device generates a quantified value based on the light collected from the animal.

2. An apparatus as recited in claim 1, wherein the animal is not anesthetized.

3. An apparatus as recited in claim 1, wherein the light monitoring device is configured to collect light over substantially the entire surface area of the body and the head of the animal in less than 60 seconds.

4. An apparatus as recited in claim 1, wherein the light monitoring device comprises a plurality of sensors arranged over various overlapping areas of the animal.

5. An apparatus as recited in claim 4, wherein the light monitoring device further comprises a first movement mechanism for moving the sensors over the surface area of the animal.

6. An apparatus as recited in claim 4, wherein the light monitoring device further comprises:

a second movement mechanism for positioning the sensors with respect to the animal so that the animal is in either a first position wherein the sensors can collect light from the animal or a second position wherein the sensors cannot collect a substantial portion of the light from the animal; and a restrainer for holding the animal in a substantially fixed, resting horizontal position while the animal is positioned in the first position and the sensors are collecting light from the animal.

7. An apparatus for collecting light emitted from an animal, where a luminescent reporter has been injected into the animal, the apparatus comprising:

a chamber for receiving the animal, wherein the chamber is light tight preventing a substantial portion of outside room light from entering the chamber and interfering with light emitted from the animal when the chamber is closed and the animal is inside the chamber;

a light monitoring device for collecting light from different portions of the animal when the animal is inside the closed chamber, wherein the light monitoring device is arranged to collect light over a substantially entire surface area of the body and head of the animal;

a first movement mechanism and a second movement mechanism for positioning the light monitoring device with respect to the animal so that the animal is in either a first position wherein the sensors can collect light from the animal or a second position wherein the sensors cannot collect a substantial portion of the light from the animal; and a restrainer for holding the animal in a substantially fixed, resting horizontal position while the animal is positioned in the first position and the sensors are collecting light from the animal, wherein the first movement mechanism is a rotation motor for rotating the sensors around the longitudinal axis of the animal while the animal is held by the restrainer and after the animal is positioned in the first position by the second movement mechanism, wherein the second movement mechanism is a translation motor.

8. An apparatus as recited in claim 6, wherein the first position is a position between the sensors.

9. An apparatus as recited in claim 6, wherein the restrainer is formed from a material that can be sterilized at high temperatures and high pressure.

10. An apparatus as recited in claim 9, wherein the restrainer is formed from a glass material.

11. An apparatus as recited in claim 9, wherein the restrainer comprises:
a glass tube for inserting the animal therein and holding the animal's body in a substantially fixed, resting horizontal position, wherein the glass tube includes a nose holding device which can flexibly conform to a portion of the animal's head to thereby hold the animal head in a substantially fixed, resting horizontal position; and
a tail holding portion for holding the animal's tail in a substantially fixed position.

12. An apparatus as recited in claim 11, wherein the tail holding portion includes a groove for receiving the tail of the animal and one or more straps for holding the tail within the groove.

13. An apparatus as recited in claim 4, wherein the animal is confined in a measurement chamber that is sized to constrain the animal while allowing insertion of the animal into the measurement chamber, in which the animal is positioned while the sensors are collecting light emitted.

14. An apparatus as recited in claim 4, wherein each sensor is selected from a group consisting of a photo multiplier tube (PMT), a silicon photodiode, an avalanche photodiode (APD), and a hybrid PMT.

15. An apparatus as recited in claim 14, wherein the sensors are staggered along the longitudinal axis of the animal.

16. An apparatus as recited in claim 15, wherein the sensors are spaced an equal distance apart around the longitudinal axis of the body and head of the animal.

17. An apparatus as recited in claim 16, wherein there are three sensors spaced 120 degrees apart.

18. A method of collecting light emitted from an animal, where a luminescent reporter has been injected into the animal, comprising:

placing the animal within a restrainer into a light tight chamber so that the animal is held in a substantially fixed, resting horizontal position;

moving a plurality of detectors in the light tight chamber relative to the animal from a home position to a measurement position with a first movement mechanism and a second movement mechanism wherein the first movement mechanism is a rotation motor for rotating the plurality of detectors around the longitudinal axis of the animal while the animal is held be the restrainer and after the animal is positioned by the second movement mechanism to a position where the detectors can collect light from the animal, wherein the second movement mechanism is a translation motor;

launching a 360 degree rotation of the detectors around the animal; and obtaining a quantitative measurement based on light detected by the detectors.

19. A method as recited in claim 18, after the detectors are launched, they detect light continuously as the detectors rotate 360 degrees around the animal.

20. A method as recited in claim 18, after the detectors are launched, they detect light at discrete positions around the 360 degrees, wherein movement of the detectors is stopped at each discrete position.

21. A method as recited in claim 18, wherein
after the detectors are launched, they detect light continuously as the detectors rotate 360 degrees around the animal when a continuous mode is selected; and
after the detectors are launched, they detect light at discrete positions around the 360 degrees, wherein movement of the detectors is stopped at each discrete position when a stepping mode is selected.

22. A method as recited in claim 18, wherein
the detectors are operated in a photon counting mode when signals to be detected are very dim, and
the detectors are operated in a current averaging mode when signals to be detected are bright and can possibly reach a level that would cause saturation in the photon counting mode.

23. A method as recited in claim 18, further comprising:
using the quantitative measurement to quantify the expression of a reporter gene or the stage of progression of cancer metastasis or infectious disease in the animal;
using the quantitative measurement for the validation of Light-Producing Transgenic Animals (LPTA), by monitoring quantitatively and precisely the expression of the targeted gene(s); or
using the quantitative measurement for screening of infectious disease and tumor models in laboratory animals, and to the drug development projects related to them.

* * * * *

UNITED STATES PATENT AND TRADEMARK OFFICE
CERTIFICATE OF CORRECTION

PATENT NO. : 7,555,334 B2 Page 1 of 1
APPLICATION NO. : 10/969230
DATED : June 30, 2009
INVENTOR(S) : Coquoz et al.

It is certified that error appears in the above-identified patent and that said Letters Patent is hereby corrected as shown below:

IN THE SPECIFICATION:

Col. 6, line 25, change "breath" to --breathe--.

Col. 7, line 22, change "degress" to --degrees--.

CLAIMS:

Col. 12, line 10, Claim 18, change "be" to --by--.

Signed and Sealed this

Sixteenth Day of February, 2010

David J. Kappos
*Director of the United States Patent and Trademark Office*